United States Patent [19]

Sumino et al.

[11] Patent Number: 5,463,075
[45] Date of Patent: Oct. 31, 1995

[54] PROCESS FOR PREPARING 1,2-PYRAZOLIDINE-4-YL-DISULFIDE COMPOUND

[75] Inventors: Motoshige Sumino; Tsutomu Tani; Atsunori Sano, all of Kawagoe, Japan

[73] Assignee: WAKO Pure Chemical Industries, Ltd., Kawagoe, Japan

[21] Appl. No.: 300,808

[22] Filed: Sep. 6, 1994

[30] Foreign Application Priority Data

Sep. 6, 1993 [JP] Japan .................................. 5-245910

[51] Int. Cl.⁶ .................................................. C07D 231/04
[52] U.S. Cl. ........................................................ 548/365.1
[58] Field of Search ............................. 548/365.1; 568/21

OTHER PUBLICATIONS

Houben–Weyl, *Method, der Organ. Chemie*, vol. 9, (1955), pp. 65, 66.

*Primary Examiner*—Robert W. Ramsuer
*Attorney, Agent, or Firm*—Foley & Lardner

[57] ABSTRACT

Novel and improved simple process for preparing a 1,2-pyrazolidine-4-yl-disulfide compound represented by the following formula:

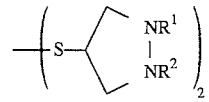

wherein $R^1$ and $R^2$ are, independently each other, a hydrogen atom or an amino-protecting group.

This compound may be prepared by reacting a compound of the formula:

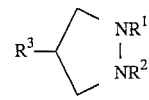

wherein $R^3$ is an acid anion residue group, and $R^1$ and $R^2$ have the same meanings as above, with a disulfide compound selected from the group consisting of an alkali metal disulfide, an alkali earth metal disulfide, an ammonium disulfide and a tri-alkylammonium disulfide.

5 Claims, No Drawings

PROCESS FOR PREPARING 1,2-PYRAZOLIDINE-4-YL-DISULFIDE COMPOUND

BACKGROUND OF THE INVENTION

1. Field of the Invention

The present invention relates to a process for preparing a 1,2-pyrazolidine-4-yl-disulfide compound represented by the following formula:

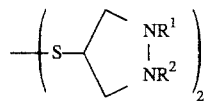

(II)

wherein $R^1$ and $R^2$ are, independently each other, a hydrogen atom or an amino-protecting group, which is a useful intermediate for producing 6,7-dihydro-6-mercapto-5H-pyrazolo[1,2-a][1,2,4] triazolium.

2. Description of the Prior Art

Heretofore, there have been proposed carbapenem antibiotics which possess potent antimicrobial activity with a broad spectrum, and they have been used in clinical practice. For example, Japanese Laid-Open Patent Publication No. 230,286/1992 discloses (1R,5S,6S)-2-[(6,7-dihydro-5H-pyrazolo[1,2-a][1,2,4] triazolium-6-yl)]thio-6-[(R)-1-hydroxyethyl]-1-methyl-carbapenum-3-carboxylate as one of such carbapenem compounds.

This carbapenem compound may be prepared by using a mercapto reagent, 6,7-dihydro-6-mercapto-5H-pyrazolo[1,2-a][1,2,4]-triazolium derivative of the following formula:

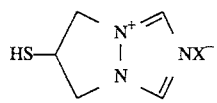

wherein $X^-$ is an anion charge. In the above patent publication, this mercapto reagent is prepared by the following Reaction Scheme [A].

Reaction Scheme [A]

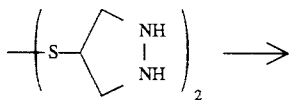

[IIa]

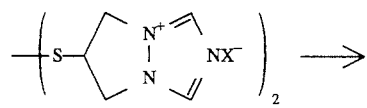

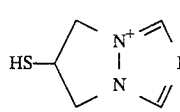

In the Reaction Scheme [A], the only process for preparing the starting disulfide compound of the formula (IIa) is disclosed in Japanese Laid-Open Patent Publication No. 230,267/1992. The following Reaction Scheme [B] shows the process.

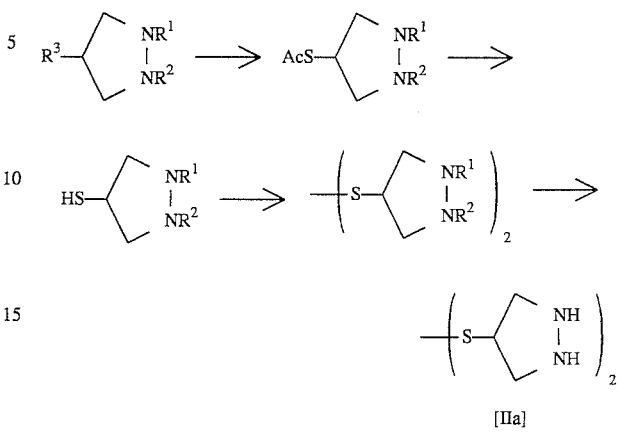

wherein $R^3$ is bromine atom. However, the process comprises as many as four reaction steps from the starting compound, that is, 1) thioacetylation, 2) hydrolysis, 3) oxidation, and 4) deprotection. Furthermore, the second reaction step gives rise to a thiol compound, which causes irritant bad odor. In view of these disadvantages, there has been a demand for another process for preparing the compound of formula (IIa) which would be preferable and suitable for the purpose of commercial-scale production.

SUMMARY OF THE INVENTION

The present invention provides a novel and improved simple process for preparing a 1,2-pyrazolidine-4-yl-disulfide compound which is a key starting compound for the preparation of 6,7-dihydro-6-mercapto-5H-pyrazolo [1,2-a][1,2,4]triazolium as shown above.

In accordance with the invention, there is provided a process for preparing a 1,2-pyrazolidine-4-yl-disulfide compound represented by the following formula:

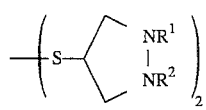

(II)

wherein $R^1$ and $R^2$ are, independently each other, a hydrogen atom or an amino-protecting group, which comprises reacting a compound of the formula:

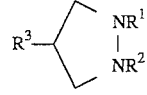

(I)

wherein $R^3$ is an acid anion residue group, and $R^1$ and $R^2$ have the same meanings as above, with a disulfide compound selected from the group consisting of an alkali metal disulfide, an alkali earth metal disulfide, an ammonium disulfide and a tri-alkylammonium disulfide, to give a compound represented by formula (II).

Through extensive investigations, the present inventors have discovered that the 1,2-pyrazolidine-4-yl-disulfide of formula (II) can easily be produced in good yields by reacting the compound of the formula (I) with a disulfide compound.

DETAILED DESCRIPTION OF THE INVENTION

In the specification of the present application, the term "an amino-protecting group" represented by $R^1$ and $R^2$ stands for groups usually employed in peptide chemistry, for example, aromatic acyl groups such as benzoyl, phthaloyl, phenoxyacetyl which may be substituted by halogen, nitro, a lower alkyl or a lower alkoxy; acyl derived from aliphatic or halogenated aliphatic carboxylic acid such as formyl, acetyl, propionyl, butyryl, haloacetyl (e.g. chloroacetyl, bromoacetyl) or the like; acyl derived from sulfonic acid such as methanesulfonyl, trifluoromethanesulfonyl, camphorsulfonyl, benzenesulfonyl which may be substituted by halogen, nitro, a lower alkyl or a lower alkoxy; esterified carboxyl groups such as methoxycarbonyl, ethoxycarbonyl, tert-butoxycarbonyl, allyloxycarbonyl, benzyloxycarbonyl which may be substituted by halogen, nitro, a lower alkyl or a lower alkoxy; aralkyl such as benzyl, phenethyl, etc. which may be substituted by halogen, nitro, a lower alkyl or a lower alkoxy; carbamoyl groups such as methylcarbamoyl, ethylcarbamoyl, phenylcarbamoyl.

The term "acid anion residue" represented by $R^3$ may be, in a broader sense, a residue derived from proton donor by eliminating the proton. These proton donor may include, for example, an organic acid, that is, lower aliphatic acid such as acetic acid, propionic acid, butyric acid, trifluoroacetic acid or the like; benzoic acid which may be substituted by halogen, nitro, a lower alkyl or a lower alkoxy; alkylsulfonic acid (e.g. methanesulfonic acid), halogenated lower alkylsulfonic acid (e.g. trifluoromethanesulfonic acid); benzenesulfonic acid which may be substituted by halogen, nitro, a lower alkyl or a lower alkoxy; organic phosphinic acid such as dimethylphosphinic acid, diethylphosphinic acid, diphenylphosphinic acid; and inorganic acid such as sulfuric acid, nitrous acid, nitric acid, phosphoric acid, hydrochloric acid, hydrobromic acid, hydroiodic acid, perchloric acid, hydrofluoroboric acid or the like.

The term "lower", used throughout the present specification and claims to qualify a group or a compound, means that the group or compound so qualified contains 1 to 6 carbon atoms. The alkyl or alkoxy may be a linear, branched or cyclic ones.

The disulfide compound to be reacted with the compound of the formula (I) in the present invention may be alkali metal disulfide such as lithium disulfide, sodium disulfide, potassium disulfide; alkali earth metal disulfide such as magnesium disulfide, calcium disulfide; ammonium disulfide; trialkylammonium disulfide such as trimethylammonium disulfide, triethylammonium disulfide or the like. Among them, alkali metal disulfide such as lithium disulfide, sodium disulfide and potassium disulfide or ammonium disulfide is prefarably used.

The amount of the disulfide compound to be used in the reaction with the compound of formula (I) of the present invention is not limited; however, in general it is conveniently more than 1 mole amount, preferably from 1.0 mole amount to 1.5 mole amount per mole of the compound of formula (I). The reaction of the compound of formula (I) with the disulfide compound may be carried out in the presence of a solvent. The solvent which can dissolve the disulfide compound or the compound of the formula (I) even in a small amount may be used in this reaction. Examples of such a solvent include water; alcohols such as methanol, ethanol or the like; amides such as formamide, dimethylformamide or the like; ethers such as tetrahydrofuran, dioxane, dimethoxyethane or the like; nitriles such as acetonitrile, propionitrile or the like; or the combination of these solvents. Among them, water or alcohols, or the mixture of these solvents is preferably used in view of the cost performances.

The reaction temperature of the present invention process is not limited to a particular range and may vary from room temperature to a temperature near the boiling point of the Solvent; however, the reaction is suitably carried out at a temperature near the boiling point of the solvent. Usually, the reaction may be finished in a time ranging from a few minutes to a few days according to the reaction temperature, and the endpoint of this reaction can easily be monitored by HPLC method.

A disulfide compound to be used in the present invention can be prepared by reacting a sulfide compound with sulfur. For example, in accordance with the method as disclosed in Reagents for Organic Synthesis (John Wiley and Sons, Inc.), vol. 1, page 1064–1065 (1967), it can be prepared by reacting a sulfide compound such as sodium sulfide or potassium sulfide with an equivalent mole of sulfur in an appropriate solvent. In detail, a disulfide compound can easily be prepared by reacting 1 mole amount of sulfide with 1 to 1.5 mole amount of sulfur in an appropriate solvent such as the one which may be used for the next reaction, at a temperature ranging from room temrerature to a temperature near the boiling point of the solvent. The resulting disulfide compound may be isolated from the reaction mixture by usual method such as concentration of the solvent or crystalization or the like; however, it is preferable to use the reaction mixture without isolation of the compound.

1,2-Pyrazolidine-4-yl-disulfide of formula (II) of the present invention, thus obtained by the reaction between the compound of formula (I) and a disulfide compound, may be used by being isolated from the reaction mixture by usual manner such as concentration of the reaction solvent or crystalization or the like, or without being isolated. For example, when the compound of formula (II) has amino-protecting group(s) (either or neither $R^1$ or $R^2$ is hydrogen), isolation from the reaction mixture is not necessary for the next step to remove the protecting group, and when the compound has no amino-protecting group (both of $R^1$ and $R^2$ are hydrogen), isolation from the reaction mixture is unnecessary, too, for the reaction to synthesize 6,7-dihydro-6-mercapto-5H-pyrazolo[1,2-a][1,2,4]-triazolium. For the purpose of commercial-scale production, it is preferable to use the compound of formula (II) without isolation from the reaction mixture.

The compound of formula (I) to be employed as a starting compound in the present invention may be prepared in such a manner as disclosed in Japanese Laid-Open Patent Publication No.67,269/1990, for example, as shown in the following Reaction Scheme [C].

Reaction Scheme [C]

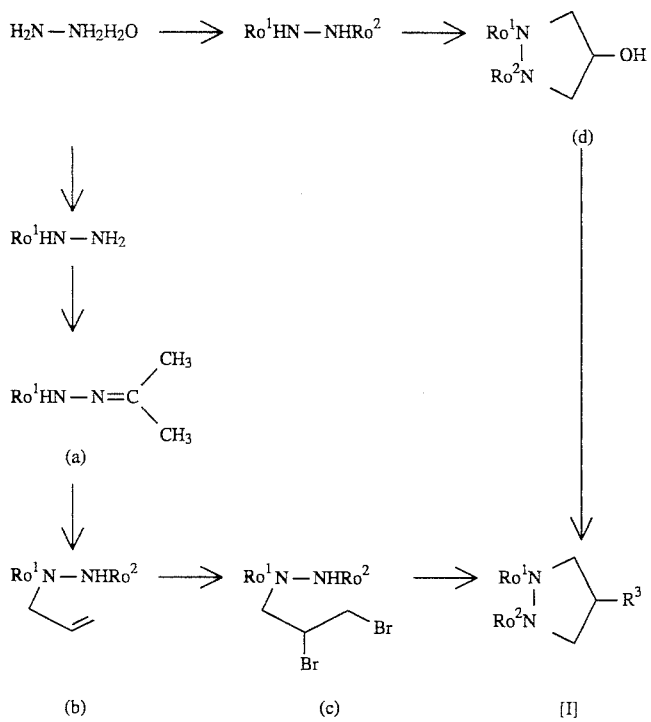

wherein $R_o^1$ and $R_o^2$ are, independently each other, an amino-protecting group and $R^3$ has the same meaning as above.

For example, a commercially available hydrazine hydrate is protected by an appropriate protecting group: $(R_o^1)$, then the protected hydrazine is reacted with acetone to give hydrazone (a). The hydrazone of formula (a) is then reacted with allyl halide in the presence of a base to give an allylated compound. The resulting compound is deprotected, then again protected by appropriate protecting group(s) $(R_o^1, R_o^2)$ to give allylhydrazine (b). This allylhydrazine of formula (b) is halogenated with bromine or chlorine to give dihoalogenated compound of formula (c), then the resulting compound of formula (c) is treated with a base such as potassium carbonate to give the compound of formula (I) in which $R^3$ is a halogen. On the other hand, a commercially available hydrazine hydrate is protected by appropriate protecting group(s) $(R_o^1, R_o^2)$, then the protected hydrazine is reacted with epichlorohydrin to give an alcohol compound of formula (d). The compound of formula (d) is then treated with acid chloride such as methenesulfonyl chloride to give the compound of formula (I) in which $R^3$ is acid residue group.

If necessary, the protecting group(s) $(R_o^1, R_o^2)$ of the compound of formula (I) can easily be removed.

EXAMPLES

The following examples illustrate the present invention more specifically. It should be noted; however, that the invention is never limited to those examples alone.

Example 1

To a mixture solution of 1.15 g (25 mM) of lithium sulfide in 50 ml of water was added 0.8 g (25 mM) of sulfur, and the reaction mixture was heated at 80°–90° C. for 1 hour under stirring. To this reaction mixture was added a solution obtained by reacting 4.15 g (30 mM) of potassium carbonate with 9.37 g (50 mM) of 4-bromo-1,2-pyrazolidine hydrochloride in 50 ml of water, and the reaction mixture was stirred for 1 hour at the same condition. After cooling, the reaction mixture was adjusted to pH 5–6 with acetic acid and extracted with methylene chloride. The organic layer was dried over magnesium sulfate and the solvent was removed under reduced pressure. The resulting residue was dissolved in methanol and then conc.HCl was added to this methanol solution. The precipitated crystals were collected by filtration to give 5.2 g (75% yield) of 1,2-pyrazolidine-4-yl-disulfide dihydrochloride salt.

$^1$H-NMR $(D_2O)\delta$ ppm: 3.46–3.52 (4H, m), 3.65–3.73 (4H, m), 4.06–4.11 (2H, m).

Example 2

1,2-Pyrazolidine-4-yl-disulfide dihydrochloride salt was obtained by repeating the Example 1 except that 6 g (25 mM) of sodium sulfide 9-hydrate was used instead of 1.15 g (25 mM) of lithium sulfide.

Yield: 4.8 g (69% yield).

Example 3

1,2-Pyrazolidine-4-yl-disulfide dihydrochloride salt was obtained by repeating the Example 1 except that 2.76 g (25 mM) of potassium sulfide was used instead of 1.15 g (25 mM) of lithium sulfide.

Yield: 5.5 g (79% yield).

Example 4

1,2-Pyrazolidine-4-yl-disulfide dihydrochloride salt was obtained by repeating the Example 1 except that 8.52 g (25 mM) of 20% ammonium sulfide solution was used instead of 1.15 g (25 mM) of lithium sulfide.

Yield: 3.6 g (52% yield).

Example 5

To a solution of 12.5 mM of potassium disulfide solution which was obtained by repeating the Example 3 was added a solution of 4.48 g (25 mM) of 1-formyl-4-bromo-1,2-pyrazolidine in 50 ml of water, then the reaction mixture was stirred for 1 hour at 80°–90° C. After cooling, the reaction mixture was extracted with methylene chloride, and the organic layer was dried over magnesium sulfate and the solvent was removed under reduced pressure. The resulting residue was treated in the same manner as described in Example 1 to give 1.90 g (65% yield) of di-(1-formyl-1,2-pyrazolidine-4-yl) disulfide.

$^1$H-NMR (CDCl$_3$)δ ppm: 3.22 (4H, d), 3.43 (2H, dd), 3.78–3.85 (2H, m), 3.93–3.98 (2H, m), 4.54 (2H,bs), 8.44 (2H, s).

Example 6

A mixture solution of 2.76 g (25 mM) of potassium sulfide and 0.8 g (25 mM) of sulfur in 50 ml of ethanol was refluxed for 1 hour under stirring. To this reaction mixture was added a solution of 5.18 g (25 mM) of 1,2-diformyl-4-bromo-1,2-pyrazolidine in 50 ml of ethanol, and the reaction mixture was stirred for 1 hour at the same condition. After reaction, ethanol was removed under reduced pressure and the resulting residue was dissolved in methylene chrolide. The unsolved substance was removed by filtration, and the filtrate was removed to give 2.28 g (55% yield) of di-(1,2-diformyl-1,2-pyrazolidine-4-yl) disulfide.

Example 7

A mixture solution of 2.76 g (25 mM) of potassium sulfide and 0.8 g (25 mM) of sulfur in 50 ml of ethanol was refluxed for 1 hour under stirring. To this reaction mixture was added a solution of 5.18 g (25 mM) of 1,2-diformyl-4-bromo-1,2-pyrazolidine in 50 ml of ethanol, and the reaction mixture was stirred for 1 hour at the same condition. After reaction, the reaction mixture was cooled, and 5 ml of conc.HCl was added to this solution, and the mixture was stirred for 2 hours at 40° C. The precipitated crystals were collected by filtration and washed with ethanol to give 4.2 g (61% yield) of 1,2-pyrazolidine-4-yl-disulfide dihydrochloride salt.

Example 8

A mixture solution of 2.76 g (25 mM) of potassium sulfide and 0.8 g (25 mM) of sulfur in 50 ml of ethanol was refluxed for 1 hour under stirring. To this reaction mixture was added a solution of 6.36 g (25 mM) of 1,2-diformyl-4-methylsulfonyloxy-1,2-pyrazolidine in 50 ml of ethanol and the reaction mixture was stirred for 1 hour at the same condition.

After cooling the reaction mixture, 5 ml of conc.HCl was added to this solution and the mixture was stirred for 2 hours at 40° C. The precipitated crystals were collected by filtration and washed with ethanol to give 3.2 g (47% yield) of 1,2-pyrazolidine-4-yl disulfide dihydrochloride salt.

What we claim is:

1. A process for preparing a 1,2-pyrazolidine-4-yl-disulfide compound represented by the following formula:

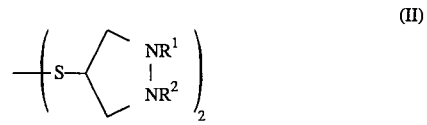

wherein $R^1$ and $R^2$ are, independently each other, a hydrogen atom or an amino-protecting group, which comprises reacting a compound of the formula:

wherein $R^3$ is an acid anion residue group, and $R^1$ and $R^2$ have the same meanings as above, with a disulfide compound selected from the group consisting of an alkali metal disulfide, an alkali earth metal disulfide, an ammonium disulfide and a tri-alkylammonium disulfide, to give a compound represented by formula (II).

2. A process according to claim 1 wherein the disulfide compound is prepared by reacting a sulfide compound with sulfur, and the resulting disulfide compound is used without isolation from the reaction mixture.

3. A process according to claim 1 wherein the disulfide compound is selected from the group consisting of lithium disulfide, sodium disulfide, potassium disulfide and ammonium disulfide.

4. A process according to claim 2 wherein the disulfide compound is selected from the group consisting of lithium disulfide, sodium disulfide, potassium disulfide and ammonium disulfide.

5. The process as claimed in claim 1, wherein $R^1$ and $R^2$ are both hydrogen.

\* \* \* \* \*

UNITED STATES PATENT AND TRADEMARK OFFICE
CERTIFICATE OF CORRECTION

PATENT NO.   : 5,463,075
DATED        : October 31, 1995
INVENTOR(S)  : Motoshige SUMINO et al.

It is certified that error appears in the above-indentified patent and that said Letters Patent is hereby corrected as shown below:

Title page item, [73] Assignee: should read --and LEDERLE (JAPAN), LTD., Tokyo, Japan--.

Signed and Sealed this

Fourth Day of February, 1997

Attest:

Attesting Officer

BRUCE LEHMAN

Commissioner of Patents and Trademarks